(12) United States Patent
Longo et al.

(10) Patent No.: US 12,295,657 B2
(45) Date of Patent: May 13, 2025

(54) METHOD FOR ALTERING THE VISUAL PERFORMANCE OF A SUBJECT, METHOD FOR MEASURING THE SPHERICAL REFRACTION CORRECTION NEED OF A SUBJECT AND OPTICAL SYSTEM FOR IMPLEMENTING THESE METHODS

(71) Applicant: Essilor International, Charenton-le-pont (FR)

(72) Inventors: Adèle Longo, Charenton-le-pont (FR); Marc Vincent, Charenton-le-pont (FR); Helene Starynkevitch, Charenton-le-pont (FR)

(73) Assignee: Essilor International, Charenton-le-pont (FR)

( * ) Notice: Subject to any disclaimer, the term of this patent is extended or adjusted under 35 U.S.C. 154(b) by 1014 days.

(21) Appl. No.: 16/970,575

(22) PCT Filed: Feb. 22, 2019

(86) PCT No.: PCT/EP2019/054498
§ 371 (c)(1),
(2) Date: Aug. 17, 2020

(87) PCT Pub. No.: WO2019/162476
PCT Pub. Date: Aug. 29, 2019

(65) Prior Publication Data
US 2021/0106216 A1   Apr. 15, 2021

(30) Foreign Application Priority Data
Feb. 23, 2018   (EP) .................................. 18305195

(51) Int. Cl.
*A61B 3/00*   (2006.01)
*A61B 3/028*   (2006.01)
*A61B 3/032*   (2006.01)

(52) U.S. Cl.
CPC .......... *A61B 3/0025* (2013.01); *A61B 3/0033* (2013.01); *A61B 3/0041* (2013.01); *A61B 3/0285* (2013.01); *A61B 3/032* (2013.01)

(58) Field of Classification Search
CPC ..... A61B 3/032; A61B 3/0285; A61B 3/0041; A61B 3/0033; A61B 3/0025; A61B 3/04;
(Continued)

(56) References Cited

U.S. PATENT DOCUMENTS 5,677,750 A * 10/1997 Qi .......................... G09B 23/28
351/205
2006/0164599 A1   7/2006 Ikezawa
(Continued)

FOREIGN PATENT DOCUMENTS

CN   107209399 A   9/2017
EP   3 175 776 A1   6/2017
(Continued)

OTHER PUBLICATIONS

International Search Report for PCT/EP2019/054498 mailed Jun. 7, 2019, 4 pages.
(Continued)

*Primary Examiner* — Brandi N Thomas
(74) *Attorney, Agent, or Firm* — NIXON & VANDERHYE

(57) ABSTRACT

Disclosed is a method for altering the visual performance of a subject using an optical system arranged in front of at least one eye of the subject, and including: b) determining an optotype; c) displaying the optotype to the subject in such a way that it is visible by the subject through the optical system; d) assessing the visual performance of the subject viewing the optotype through the optical system; and e) adding a positive or negative altering value of spherical optical power to the optical system. The method includes,
(Continued)

before step b): a) choosing a target value of visual performance; and in that, at step b), the optotype has a size which is determined depending on the target value of visual performance; at step e), the altering value of spherical optical power is determined depending on the target value of visual performance.

21 Claims, 5 Drawing Sheets

(58) Field of Classification Search
CPC ....... A61B 3/103; A61B 3/0091; A61B 3/028; A61B 3/036; A61B 3/0016; A61B 3/0075; A61B 3/0008; A61B 3/113; A61B 3/005; A61B 3/09; A61B 3/10; A61B 3/1015; A61B 3/152; A61B 5/11; A61B 1/00057; A61B 2560/0233; A61B 3/0058; A61B 3/0083; A61B 3/02; A61B 3/024; A61B 3/1035; A61B 3/11; A61B 3/14; A61B 3/145; A61B 5/0002; G02C 2202/22; G02C 7/044; G02C 11/10; G02C 2202/12; G02C 2202/16; G02C 2202/18; G02C 2202/20; G02C 2202/24; G02C 7/02; G02C 7/022; G02C 7/041; G02C 7/049; G02C 7/06; G02C 7/061; G02C 7/066; G02C 7/08; G02C 7/083; G02C 7/101; G02C 7/102
See application file for complete search history.

(56) References Cited

U.S. PATENT DOCUMENTS

| | | |
|---|---|---|
| 2016/0370602 A1 | 12/2016 | Fujikado et al. |
| 2017/0127933 A1* | 5/2017 | Widman .............. A61B 3/0285 |
| 2017/0209039 A1 | 7/2017 | Myagkikh |
| 2017/0261767 A1 | 9/2017 | Ohlendorf et al. |

FOREIGN PATENT DOCUMENTS

| | | |
|---|---|---|
| FR | 3 050 922 | 11/2017 |
| JP | 2006-198286 A | 8/2006 |
| JP | 2007-531559 A | 11/2007 |
| JP | 2016-200762 A | 12/2016 |
| JP | 2017-099640 A | 6/2017 |
| KR | 20160146987 A | 12/2016 |
| WO | 2005/079546 A2 | 9/2005 |

OTHER PUBLICATIONS

Written Opinion of the ISA for PCT/EP2019/054498 mailed Jun. 7, 2019, 13 pages.
Office Action issued in Chinese Patent Application No. 201980012822.2 dated Feb. 28, 2023.
Chen et al., "Comparative analysis between 1387 cases of medical optometry and 1176 cases of conventional optometry for refraction errors," Sichuan Medical Journal, 2004, vol. 25, No. 3, pp. 347-248.
Office Action issued in Japanese Patent Application No. 2020-544294 dated Nov. 21, 2022.
Office Action, issued in Korean Patent Application No. 10-2020-7022323 dated Dec. 22, 2023.

* cited by examiner

METHOD FOR ALTERING THE VISUAL PERFORMANCE OF A SUBJECT, METHOD FOR MEASURING THE SPHERICAL REFRACTION CORRECTION NEED OF A SUBJECT AND OPTICAL SYSTEM FOR IMPLEMENTING THESE METHODS

This application is the U.S. national phase of International Application No. PCT/EP2019/054498 filed Feb. 22, 2019 which designated the U.S. and claims priority to EP patent application Ser. No. 18/305,195.2 filed Feb. 23, 2018, the entire contents of each of which are hereby incorporated by reference.

TECHNICAL FIELD OF THE INVENTION

The invention is related to a method for altering the visual performance of a subject and, in particular, for the assessment of the visual acuity of that subject and more specifically when determining an optical correction level for the vision of that subject during a test that may require blurring and/or unblurring the vision of the subject.

BACKGROUND INFORMATION AND PRIOR ART

When assessing the refraction of each eye in subjective tests involving trials of reading of optotypes and visual targets, it is important to control the accommodation of the eyes so as to avoid erroneous assessment of the subjective refraction of the subject, the subject using accommodation to focus on the target and answer correctly to the tests.

The common way to control the accommodation is the so called blurring or fogging method (these are synonyms) in which, in an initial phase of blurring, the eye is put in myopic condition with a blurring lens during the test. Then, in the following unblurring phase, correction lenses are sequentially used for unblurring the vision till the best focusing/best reading of optotypes is obtained. As a result, a value of a sphere for correction is obtained and later used to shape a corrective lens.

However, this is not an optimal method and it is time consuming because, inter alia, it does not consider the initial visual performance level as a starting point for the blurring phase nor the final visual performance to reach at the end of the unblurring phase and that could be obtained from a refraction given by corrective lenses the subject may already possess or from the objective refraction error that could be or could have been estimated or assessed. It does not either consider other characteristics of the subject such as the age, other visual defects, pupillary diameter, etc. . . . . In addition, this method is not much appreciated by the subject due to the imposed blurring.

Other accommodation control methods are known such as, for instance, the use of cyclopegic collyrium to disable the accommodation. However, this may be dangerous, it cannot be used by all practitioners and it does not always give reliable results, in particular with children.

The use of a blurring lens in front of the eye to be tested as discussed above in a fogging then defogging method is a standard method with two possible ending goals: the best focusing/best reading of optotypes with the maximum spherical optical power as discussed above or a predefined visual acuity (i.e.: 0.1 log MAR, 0.0 log MAR, −0.1 log MAR).

The visual acuity may be scored with reference to the Logarithm of the Minimum Angle of Resolution. A subject who can distinguish details as small as 1 minute of visual angle has a visual acuity of 0 log MAR, since the base 10 logarithm of 1 is 0. A subject who can distinguish details as small as 2 minutes of visual angle has a visual acuity of 0.3 log MAR, since the base 10 logarithm of 2 is near-approximately 0.3, and so on.

In short, the formula used for determining the visual acuity in log MAR is $$VA(\log MAR) = \log(\text{Minimum Angle of Resolution of the eye of the subject}).$$

An advantage of using the log MAR unit to quantify the acuity is that the increase of the acuity follows the decrease of the size of the optotypes and thus the increase in the difficulty for the subject to identify the optotype All those blurring and/or unblurring methods have drawbacks with regards to the subject doing the test but also in relation to the quality of the results which depends on the operator who uses those methods.

SUMMARY OF THE INVENTION

It is here proposed simple blurring and/or unblurring processes in which a target visual performance is taken into account to determine a size of an optotype displayed in front of the subject, and to determine the value of a spherical optical power of an optical component placed in front of the subject to alter his vision in order to blur or unblur it.

The method for altering the visual performance of a subject according to the invention may indeed be implemented as a blurring method or an unblurring method. It may also be implemented as part of a method using both a blurring and an unblurring step. In this last case, the method for altering the visual performance of the subject may be used in each of the blurring and unblurring steps or in only one of the blurring and unblurring steps.

In the case where the method for altering the visual performance of the subject is used as a blurring process according to the invention, the initial blurring phase is done considering the visual characteristics of the subject for giving to the subject a predetermined visual performance at the end of this blurring phase.

In such a blurring phase, the visual performance is of course degraded for the subject to be blurred for relaxing his/her accommodation.

During an optional further unblurring phase, the number of trials, or steps to reach the target visual performance for unblurring, would be advantageously reduced compared to the standard method, because the previous initial blurring phase was optimized. Secondly, one uses correction lenses having unequal correction gradient/difference levels in the iterative use of correction lenses for the trials, the correction gradient/difference diminishing progressively toward the end of the unblurring iterations, which brings more precision to the method. This also allows reducing the number of trials with preferably only two or three trials in the unblurring phase according to the invention.

It is also advantageous that the subject perceives an improvement of his vision at each step of the unblurring phase. In the classical refraction process, the decrease of the blur is done through identical steps, which is not easily perceived by the subject. The method according to the invention has therefore better chances to be well accepted by the subject.

In the blurring (or fogging) phase, a predefined defocusing goal to attain is chosen for the subject, an optotype is arranged in front of the subject, and the vision of the subject is defocused by placing a lens with a defocusing power in front of the eye of the subject. The predefined defocusing goal corresponds to a defocusing level target for the eye of the subject. This defocusing level target corresponds to a defocusing power target of the lens that should be placed in front of the eye at the end of the blurring phase.

This may be achieved in one single step or, preferably, through an iterative method according to which the vision of the subject is defocused progressively, by progressively modifying the defocusing power of the lens placed in front of the eye of the subject, the iterative method ending when the predefined defocusing goal is attained. During this iterative method, the subject should provide answers regarding the way he/she is perceiving the optotype.

Practically, the predefined defocusing goal to attain is defined as a target visual performance in a fogged/blurred state of the vision.

This target visual performance may for example be a target visual acuity.

The optotype may be standard letters or any kind of image having high and low spatial frequencies or even images of the "vanish" kind. The evaluation of the answers may be based on a limit method, continuous or discreet, psychophysic methods, staircase method.

Contrary to the standard one-shot initial blurring phase, the initial blurring phase according to the invention may be an iterative method.

The ending of the iterative process be objectively based on a value of visual performance such as determination of the visual acuity and comparison with the target visual acuity, or subjectively based (optotype seen/recognized or not).

Preferably, in the case of the blurring phase, iteration is stopped when the optotype is not seen anymore.

The ending of the iterative process may also be programmed to be reached when a predefined defocusing goal is reached, that is, when a defocusing level of the eye is achieved or a defocusing power target is achieved in the optical system.

Such an initial blurring or fogging phase may be practiced manually or may be automated.

Contrary to the standard initial blurring or fogging phase, where the blurring phase is the same for all subjects and environmental conditions, the initial blurring phase according to the invention may be adapted to each subject and to the environmental conditions, as will be described in more details later.

The visual performance of the subject is preferably determined at each step of the method.

For the unblurring (or defogging) phase, a predefined visual performance target to attain is chosen for the subject and an optotype is arranged in front of the subject.

Then in one step or, preferably, in an iterative process, the vision of the subject is focused (in fact re-focused). This may be done progressively and iteratively, the iterative process ending when the predefined focusing goal is attained or if the maximal visual acuity is reached.

During this iterative process, the subject should provide answers regarding the way he/she perceives and reads the optotype and this may be in the form of some question-answer game.

This will allow determining the visual acuity of the subject at each step of the method.

Practically, the predefined focusing goal to attain is defined as a target visual performance that is expected when the subject will be in a corrected state. The predefined focusing goal to attain may be the best focusing/best reading of optotypes or a predefined visual acuity (i.e.: 0.2 log MAR, 0.1 log MAR, or 0.0 log MAR).

The optotype may be standard letters, numbers, symbols or any kind of significant image (that is having a meaning for the subject) having high and low spatial frequencies or even images of the "vanish" kind.

The evaluation of the answers may be based on a limit method, continuous or discreet, psychophysics methods, staircase method . . . .

The ending of the iterative process be objectively based on a value of visual performance, such as determination of the visual acuity and comparison with the target visual acuity, or subjectively based (optotype seen clearly/recognized or not). The unblurring (or defogging) phase may be practiced manually or may be automated.

More precisely, the invention is related to a method for altering the visual performance of a subject using an optical system arranged in front of at least one eye of the subject and comprising the following successive steps:
  b) determining an optotype;
  c) displaying the optotype determined in step b) to the subject in such a way that said optotype is visible by the subject through said optical system;
  d) assessing the visual performance of the subject viewing the optotype displayed in step c) through the optical system;
  e) adding an altering value of spherical optical power to the optical system, said altering value being positive or negative.

According to the invention, the method comprises, before step b):
  a) choosing a target value of visual performance; and
  at steps b) and e), said size of the optotype and said altering value of spherical optical power are determined as functions of said target value of visual performance.

In other words, at steps b) and c), said optotype has a size which is determined depending on said target value of visual performance;
  at step e), said altering value of spherical optical power is determined depending on said target value of visual performance.

Advantageously, the method further comprises:
  a step f) of assessing the visual performance of the subject after step e), and defining the result of this assessment as a current value of visual performance;
  repeating the steps c), d), e), and f) until said current value of visual performance reaches said target value of visual performance or an extremum value of visual performance, or remains stable or departs from the target value;
  and said altering value of spherical optical power added to the optical system at each step e) being determined as a function of said target value of visual performance and of said current value of visual performance determined at the previous step d).

In a preferred embodiment, the method for altering the visual performance is a method for blurring the vision of the subject.

Therefore, in this blurring method, the goal of the alteration is to blur the vision of the subject in order to relax his/her accommodation, and the altering value of spherical optical power is positive, so as to put said subject in myopic conditions, with a blurred vision and a relaxed accommodation.

Preferably, if the subject is used to wear an ophthalmic correction equipment, then said subject wears his/her ophthalmic correction equipment or his/her objective refraction as a starting point in order to recognize the optotype during step d).

Advantageously, the blurring method comprises, at step d), asking the subject whether said optotype is recognizable, visible or imperceptible through said optical system; and, at step e), adding a positive altering value of spherical optical power, said positive altering value being determined as a function of the answer of the subject, of the previously added altering value and said target value of visual performance.

Preferably, at step e), said positive altering value is different whether the subject answers that:
he/she sees and recognizes the optotype; or
he/she sees and does not recognizes the optotype, or
he/she sees and does not see if there is an optotype.

Other advantageous and non-limiting features of the blurring method according to the invention include:
the optotype is a vanish-type optotype;
at step a), said vanish-type optotype is chosen randomly, for example among the following vanish-type letters: D, H, K, N, R, S, V, and Z;
said vanish-type optotype has a size which is larger by a predefined value, for example by 0.1 log MAR, than the target value of visual performance.

The minimal angle of resolution is the smaller visual angle that can be detected by the eye. The optotype being placed at a predefined distance from the eye of the subject, for example 6 meters, its size corresponds to a visual acuity.

In practice, the visual acuity of the subject corresponds to a size of the smallest optotype identified by the subject at a predetermined fixed distance, expressed in log MAR.

When assessing acuity with vanish optotypes, the angle of resolution corresponds to the width of the line limiting the optotype. The height of the vanish optotypes is overall higher that the height of classical optotypes for the same visual acuity. The correspondence between the size of the vanish optotypes and the acuity is established for vanish optotypes in the shape of letters. A corrective factor depending on the visual acuity value has to be taken into account.

For non-letter vanish optotypes, other correction factors may be considered to deduce the visual acuity. These correction factors may depend on the visual acuity itself.

Some on these correction are described in the following papers: Shah, N.; Dakin, S. C.; Whitaker, H. L.; Anderson, R. S. *Effect of Scoring and Termination Rules on Test-Retest Variability of a Novel High-Pass Letter Acuity Chart. Investigative ophthalmology & visual science* 2014, 55, 1386-1392; Hamm, L M; Anstice, NS; and . . . B.-J. *Recognition Acuity in Children Measured Using The Auckland Optotypes. Ophthalmic and . . .* 2018; Hamm, L M; Yeoman, J P; vision, A.-N. of *The Auckland Optotypes: An Open-Access Pictogram Set for Measuring Recognition Acuity. Journal of vision* 2018.

In a particular embodiment, if it is necessary, the optotype can be randomized and/or changed after recognition.

In another embodiment, the method also comprises
f) assessing the visual performance of the subject after step e), and defining the result of this assessment as a current value of visual performance,
steps c), d), e), and f) are repeated until said current value of visual performance reaches said target value of visual performance or remains stable or departs from the target value,
said altering value of spherical optical power added to the optical system at step e) is determined as a function of said target value of visual performance and of said current value of visual performance,
the size of the optotype remaining the same while steps c), d), e), and f) are repeated.

In a particular embodiment of this blurring method, said level of defocusing and said visual performance are correlated through a mathematical formula.

This mathematical formula may take into account different models linking the visual performance and level of defocusing of the eye of the subject. The models may be built on data collected while performing the blurring/unblurring phase on subjects and/or thanks to computer learning algorithms.

For example, bias from the environment, such as reflect of light of the display screen or bad lighting conditions, may be detected and taken into account through these computer learning algorithms.

In a particular embodiment of the method, said value of the visual acuity target determined and subsequently chosen in step a) is adapted depending on one of the following:
purpose of the blurring or unblurring phase in the subject eye examination,
personal features of the subject,
environmental parameters.

In a particular embodiment of the method, said value of the visual acuity target is determined in step a) by taking into account a model linking the defocusing level of the eye to the visual performance of the eye, this model being built on data collected while performing the blurring/unblurring phase on subjects and/or thanks to computer learning algorithms.

In another preferred embodiment, the method for altering the visual performance is a method for unblurring the vision of a subject, wherein:
the effect of the alteration consists in unblurring the vision of the subject so as to reach said target value of visual performance for one or both eyes of the subject;
said optical system initially has an added altering value of spherical optical power such as the subject is initially in myopic conditions, with a blurred vision and a relaxed accommodation;
the assessment of the visual performance of the subject viewing the optotype through the optical system at step d) allows deducing a level of defocusing of the subject; and
the altering value of spherical optical power added at step e) is negative for unblurring the vision of the subject and is determined from the target value of visual performance and from said level of defocusing.

In a particular embodiment of this unblurring method, said level of defocusing and said visual performance are correlated through a mathematical formula.

Alternatively, said level of defocusing is tabulated from said visual performance.

The defocusing power of the optical system placed in front of the subject is the spherical power of the lens placed in front of the eye of the subject.

The level of defocusing is defined as the defocusing state of the eye of the subject. This defocusing level depends both on the ametropia of the eye, and on the defocusing power of the optical system. The zero defocusing level of the eye corresponds to the state of an eye with emmetropia and no lens placed in front of it. It can be obtained by placing a lens of negative spherical power in front of an eye with myopia or a positive power in front of an eye with hypermetropia for example.

According to a further embodiment of the method, it comprises:

f) assessing the visual performance of the subject after step e), and defining the result of this assessment as a current value of visual performance, steps c), d), e), and f) being repeated until said current value of visual performance reaches said target value of visual performance or remains stable or departs from the target value, said altering value of spherical optical power added to the optical system at step e) being determined depending on said target value of visual performance and of said current value of visual performance, and step b) being repeated, and at each step b), the size of the optotype being determined depending on said target value of visual performance and of said current value of visual performance.

In an embodiment of the invention, in step b), an uncertainty on the visual performance for a current defocusing power of the optical system is determined, two lines of said optotypes are determined, the number of letters or signs per line, the number of lines, the difference in size between two adjacent lines being determined based on said uncertainty on the visual acuity.

In a embodiment of the invention, said value of the visual acuity target determined in step a) is adapted depending on one of the following:

purpose of the blurring or unblurring phase in the subject eye examination, personal features of the subject, environmental parameters.

In an embodiment of the invention, said value of the visual acuity target is determined in step a) by taking into account a model linking the defocusing level of the eye to the visual performance of the eye, this model being built on data collected while performing the blurring/unblurring phase on subjects and/or thanks to computer learning algorithms.

The invention also relates to a method for measuring a spherical refraction correction need of a subject, comprising:

implementing a method for blurring the vision of said subject; and implementing a method for unblurring the vision of said subject according to the invention, said initial myopic conditions resulting from the implementation of said method for blurring, wherein:

the successively added negative altering values of spherical optical power of the successive iterations of steps e) are added up together for defining an unblurring spherical optical power; and the spherical refraction correction need is determined based on said unblurring spherical optical power.

More precisely, the successively added negative altering values of spherical optical power of the successive iterations of steps e), are added up together until said current value of visual performance reaches said target value of visual performance, or before the current value of visual performance remains stable or departs from the target value, for defining an unblurring spherical optical power; and the spherical refraction correction need is determined based on said unblurring spherical optical power.

In a preferred embodiment of the method for measuring a spherical refraction correction need, the method for blurring is one of the methods according to the invention described above.

In a particular embodiment of the method for measuring a spherical refraction correction, it comprises:

f) assessing the visual performance of the subject after step e), and defining the result of this assessment as a current value of visual performance, wherein steps c), d), e), and f) are repeated until said current value of visual performance reaches said target value of visual performance or remains stable or departs from the target value, and wherein said altering value of spherical optical power added to the optical system at step e) is determined depending on said target value of visual performance and of said current value of visual performance, wherein step b) is repeated, and at each step b), the size of the optotype is determined depending on said target value of visual performance and of said current value of visual performance.

The invention comprises a system configured for the execution of a blurring method intended to induce the relaxation of the accommodation of the eye according to the invention, said system comprising an optical device being configured to be placed in front of at least one eye of a subject and to impart an additional spherical optical power to this eye, wherein said spherical optical power can be modified.

In the same way, the invention comprises an optical system for implementing the method according to the invention, that can in particular be configured for the execution of an unblurring method according to the invention, said system comprising an optical device being configured to be placed in front of at least one eye of a subject and to impart an additional spherical optical power to this eye, wherein said spherical optical power can be modified.

The invention comprises a system configured for the successive execution of:

1) a blurring method according to the invention; and/or 2) an unblurring method according to the invention.

The invention aims at optimizing and personalizing the blurring and/or the unblurring processes. In particular, the unblurring method according to the invention allows for the unblurring while researching a specific visual performance or the maximum convex sphere giving the best visual acuity. It allows a quicker, more precise defogging thanks to the estimation of the level of defocusing made with the measure of blurred visual acuity of the subject Thanks to the method of the invention, the optical tests are optimized because it adapts in a more precise manner the blurring and/or the unblurring lenses to the subject visual perception and performance.

It also helps the acceptation of the optical tests by the subject because it is simpler, more progressive and less frustrating for the subject.

It is also possible to diminish the impact of the operator in the implementation of the tests. This minimizes the variability of the measurement of the subjective refraction. The method can be implemented and executed automatically in a dedicated system.

Finally, this new method has been developed so that the time required for the execution of the tests is shorter, in order to prevent the subject from being exhausted by a too important effort of concentration which may introduce an error in the measurement of the subjective refraction.

Contrary to known methods, an automatic method may be implemented and used at any step of a visual examination where an unblurring is recommended as a function of, that is to say, depending on, the focalization state of the subject.

DETAILED DESCRIPTION OF EXAMPLE(S)

The following description, enriched with joint drawings that should be taken as non limitative examples, will help understand the invention and figure out how it can be realized.

Figure 1:
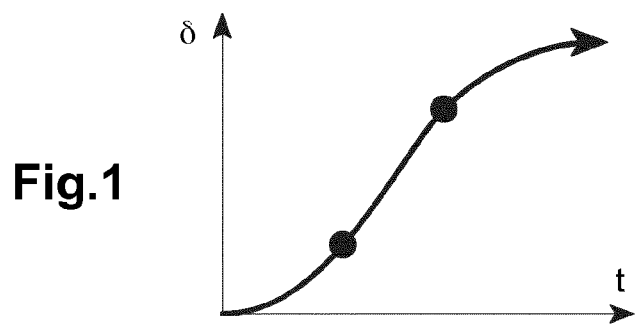
FIG. 1 represents the modification of the spherical optical power of the optical device in diopter as a function of time during iterations/steps of the method for blurring.

In the following description, the value of the defocusing will correspond to the value in diopter of the spherical optical power of the lens placed in front of the eye of the subject during the blurring or unblurring phase of the method.

This value of the defocusing power is the added value compared to the initial value of spherical optical power placed in front of the eye before the blurring or unblurring phase.

In order to help the understanding of the examples that will be described further on, the invention is now described according to a more general point of view.

According to the invention, the method for altering the visual performance of a subject using an optical system arranged in front of at least one eye of the subject comprises the following successive steps:

b) determining an optotype;

c) displaying the optotype to the subject in such a way that said optotype is visible by the subject through said optical system;

d) assessing the visual performance of the subject viewing the optotype through the optical system;

e) adding an altering value of spherical optical power to the optical system, said altering value being positive or negative;

characterized in that the method comprises, before step b):

a) choosing a target value of visual performance;

and in that, at steps c), said optotype has a size which is determined depending on said target value of visual performance;

at step e), said altering value of spherical optical power is determined depending on said target value of visual performance.

Typically, steps c), d) and e) may be repeated in several iterations.

Said method for altering the visual performance of a subject may in particular be used either in a blurring phase or in an unblurring phase of the eye test. The invention also concerns methods comprising a blurring and an unblurring phase, one of this phases at least being performed according to the invention.

The visual performance may refer to an objective or subjective feature of the vision of the subject. In particular, the visual performance may be assessed by determining the visual acuity of the subject, or by determining a level of perception relative to a specific optotype.

The level of perception may be one among three: optotype seen clearly, optotype seen blurred or optotype not seen. In the first level, the optotype is recognized without difficulty, in the second level it is recognized with difficulty and in the third level it is not recognized. The time needed by the subject to identify the optotype may determine which level of perception is reached by the subject.

The level of perception may alternatively be one among two: optotype recognized or not.

Regarding the visual acuity, any known method for determining visual acuity may be used.

Said optical system placed in front of the subject may either comprise a set of different lenses with different powers that can be alternatively or cumulatively placed in front of the eye of the subject in order to provide different spherical optical powers, or it may comprise a lens with adjustable spherical optical power, such as a liquid lens. Either way the spherical optical power of the optical system may be varied. The variation may be applied manually or through a computer controlled motorized device.

The general blurring process of the invention is the following:

1) asking the subject to look at/stare/gaze at a visual stimulus and to describe his perception of the visual stimulus;

2) modifying the level of focalization according to the personalized estimation as a function of, that is to say, depending on, the answer of the subject describing the visual stimulus;

3) having a stop criteria defining that the good/target level of defocusing or defocusing power of the optical system has been reached.

In practice, the visual stimulus is the optotype displayed in step b). The description of the perception of the visual stimulus, as detailed later, allows assessing the visual performance of the subject viewing the optotype through the optical system in step d).

In step a), a target value of visual performance is determined. It corresponds to a defocusing target: the target value of visual performance corresponds in this case to a blurred vision.

The blurring phase according to the invention may be adapted to each subject and to the environmental conditions, as will be described in more details.

In the blurring phase, the visual performance target or predefined defocusing goal may indeed be adapted depending on the purpose of this blurring phase in the subject eye examination for example.

It may be indeed different if the blurring phase is performed before performing an unblurring phase, before assessing the binocular balance or in order to determine the value of a mask for achieving a binocular refraction examination according to Humphriss method. Such a mask is used for example to inhibit central vision of one of the eyes while keeping a peripheral vision.

Before an unblurring phase, the purpose is to inhibit monocular accommodation by choosing a low visual acuity target: the visual performance target may be a visual acuity of 0.4 log MAR.

Before assessing the binocular balance of the eyes, the purpose is to ensure that the comparison of the images seen with the right and left eyes is possible: the visual performance target may be a visual acuity of $6/10^{th}$ or $8/10^{th}$.

If the blurring phase is performed to determine the value of a mask to be placed in front of a eye for achieving a binocular refraction examination according to Humphriss method: the visual performance target may be a visual acuity of $5/10^{th}$.

In the blurring phase, the visual acuity target in a blurred state may also depend on personal features of the subject, such as the age of the subject, ametropia, geographical origins of the subject and ocular history of the subject, such as ocular diseases (cataract), past prescriptions, pupil diameter etc. . . . . .

The younger the subject is, the more the eyes of the subject will have a tendency to accommodate. The visual acuity target should therefore be lower for younger subject in order to ensure accommodation relaxation.

For example, the visual acuity target could be equal to $2/10^{th}$ for children under 12 years old, $4/10^{th}$ for teenagers between 12 and 18 years old, and $6.3/10^{th}$ for adults, as the risk of accommodation is lower.

The visual acuity target for blurring may also take into account the ocular diseases such as cataract and their effect on the transparency of the eye: the visual acuity target could be $4/10^{th}$ for an older subject with cataract or $6/10^{th}$ for an older subject without cataract.

The value of the visual performance target for blurring may also be determined depending on environmental parameters, such as parameters of the measurement set-up.

Lighting conditions may for example have an impact: the contrast of the optotype and therefore its perception is modified by lighting. If the lighting conditions are low, the visual performance target is set to a lower value than the visual performance target in bright lighting conditions. Bright lighting conditions decrease the apparent contrast of the target on the screen.

As a further example, it may depend on the distance between the eye of the subject and the optical system comprising blurring/unblurring lenses and/or correction lenses placed in front of the eye of the subject.

This distance may indeed influence the optical magnification through the optical system and therefore the visual acuity determined.

A convex lens enlarges an object seen through his convex lens, whereas a concave lens shrinks the same object seen through the concave lens. In other words, the image of an object seen through a convex lens is bigger than the real object, whereas the image of an object seen through a concave lens is smaller.

The effect (enlargement or shrinkage) depends on the power and/or width of the lens, and of the distance between the lens and the eye of the subject. For example, a subject with a high degree of myopia, with a correction lens of −8 diopters placed at 20 millimeters from the eye of the subject would have a visual acuity target for blurring of about $5/10^{th}$ if the lens is placed at 10 millimeters from the eye, whereas a subject with hyperopia, the visual acuity target for blurring could be set at $8/10^{th}$ for a lens placed at 20 or 10 millimeters as the correction lens placed in front of the eye enlarges the image of the object.

Without taking into account these criteria, a mean value of $4/10^{th}$ for the visual acuity target for blurring may be used in order to relax accommodation of the subject.

In step b), an optotype is determined. In particular, the size of the optotype, associated with a corresponding visual acuity, is determined.

In the case the blurring phase, the size of the optotype is set in the first iteration of the steps c), d) and e). It is determined depending on the visual performance target. If other iterations of the steps are performed, the size of the optotype remains the same.

Therefore, in the case of the blurring phase, step c) is repeated with the same optotype.

In step d), the visual performance of the subject viewing the optotype through the optical system is assessed. For example, in step d) of the blurring phase, a current visual performance of the subject relative to the current optotype is determined.

This is done for example through a visual acuity test as described hereafter or with a subjective perception test for determining the level of perception, such as a test assessing if the letter is recognized or not recognized or seen or not seen. Any known visual perception test or acuity test may be performed.

In step e), an altering value of spherical optical power to the optical system is added, said altering value being positive.

The spherical power of the optical system place in front of the subject is therefore modified by adding an increment of positive defocusing power in front of the eye of the subject. This can be done either by adding a lens with a spherical power equal to the increment or by modifying the spherical power of a liquid lens.

The increment of spherical power added is determined depending on the visual performance target. It also takes preferably into account the current visual performance determined at step d).

Finally, this increment of spherical power is applied to the optical system in a defocusing step.

The defocusing target, and therefore the determination of the increment in spherical power of the optical system may for example be achieved taking into account any one of several models to determine the thresholds of vision: Lowery, Shah. These models are presented on the following publications: Lowery, J. P.; Hayes, J. R.; Sis, M.; Griffith, A.; Taylor, D. *Pacific Acuity Test: Testability, Validity, and Interobserver Reliability. Optometry and Vision Science* 2014, 91, 76-85 and Shah, N.; Dakin, S. C.; Whitaker, H. L.; Anderson, R. S. *Effect of Scoring and Termination Rules on Test-Retest Variability of a Novel High-Pass Letter Acuity Chart. Investigative ophthalmology & visual science,* 2014, 55, 1386-1392.

Other models may be used. Some models may be established for example by a statistical treatment of data collected while performing blurring/unblurring phases.

These models predict the visual performance, for example, the visual acuity observed in different categories of subject as a function of the defocusing power of the lens placed in front of the eye of the subject. Examples of these data are shown of FIGS. 8 and 9.

In each case, the defocusing power determined may be applied to the optical system in one step or in several steps. The advantage of applying the defocusing power in different steps is that the initial determination of the defocusing level of the eye when the vision is blurred is less accurate than the determination of the defocusing level of the eye in the subsequent steps, when the vision is less blurred. The subsequent steps allow an increased accuracy to reach the predetermined target of visual performance without going over this target.

According to the invention, the models may also be built thanks to computer learning algorithms. For example, bias from the environment, such as reflect of light of the display screen or bad lighting conditions, may be detected and taken into account through these computer learning algorithms.

Figure 7:
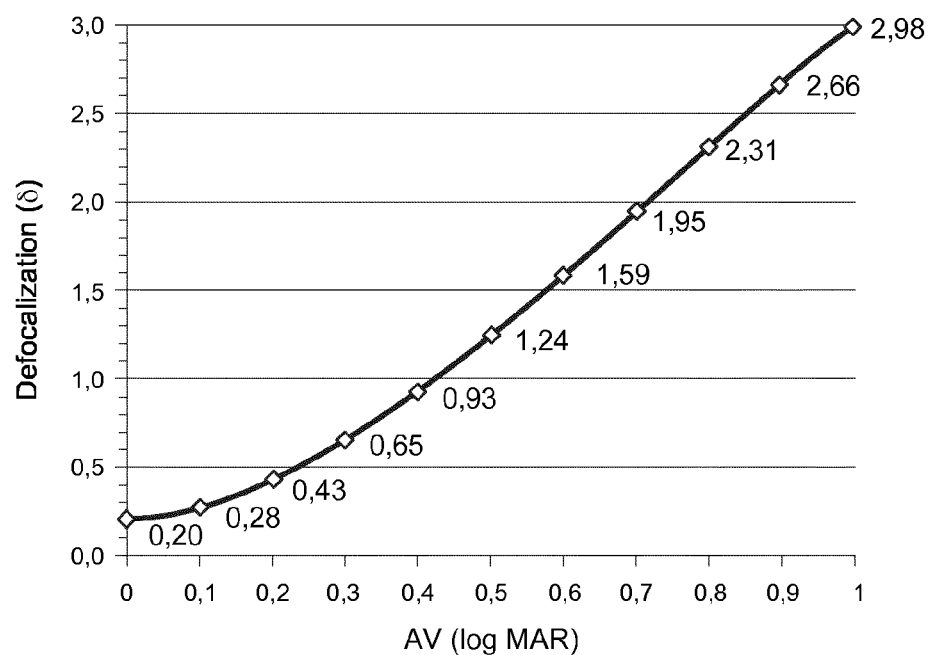
FIG. 7 represents a model of a curve with vertically the defocusing δ and horizontally the visual acuity AV (in log MAR), and that is used to compute the amount of change in optical power at each iteration/step of the method.
Figure 8:
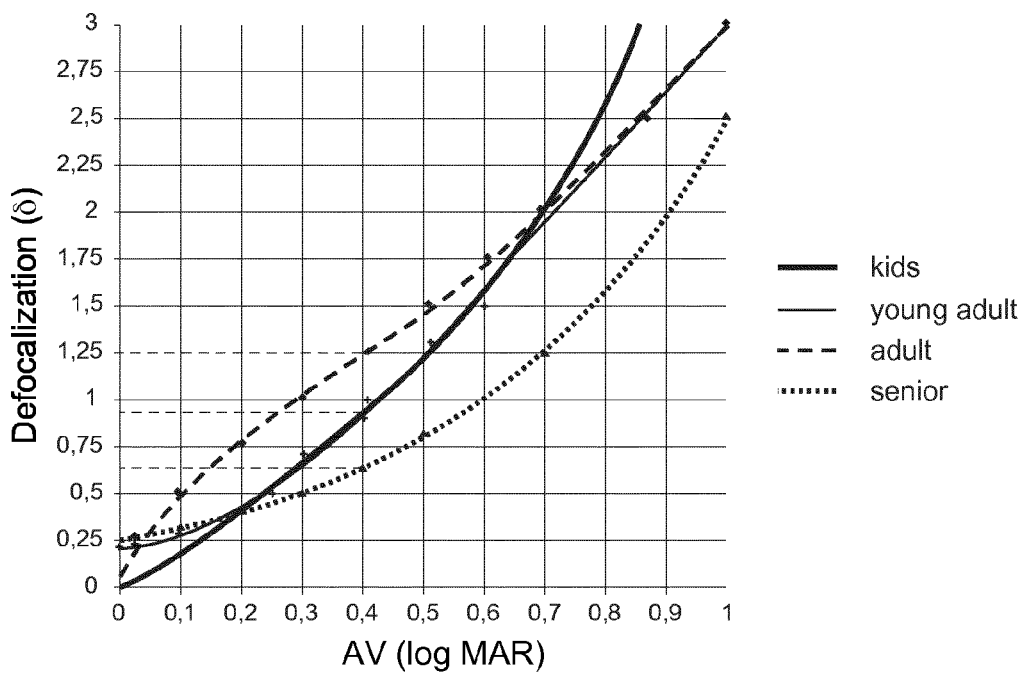
FIG. 8 represents examples of defocusing levels of the eye of the subject as a function of the corresponding visual acuity of the eye determined, for subjects being in different age categories.
Figure 9:
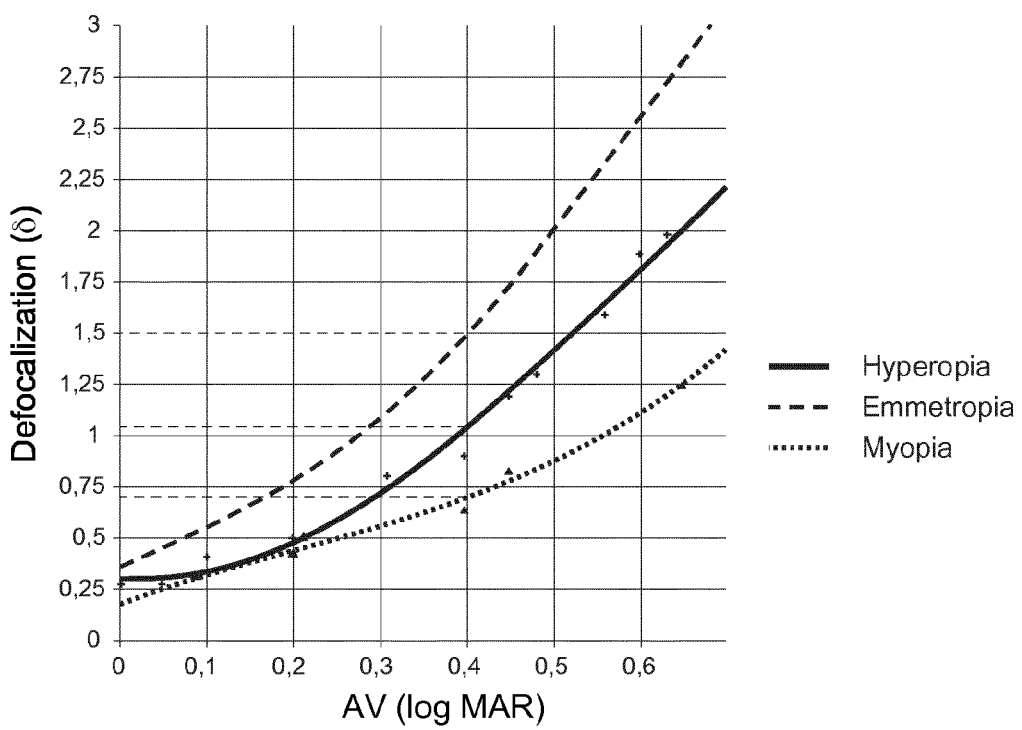
FIG. 9 represents examples of defocusing levels of the eye of the subject as a function of the corresponding visual acuity of the eye determined, for subjects having different visual defects.

Thanks to the relation established between the visual acuity and the defocusing power, through a curve such as those in FIG. 7, 8 or 9 or thanks to a table, the current defocusing level of the eye, corresponding to the current defocusing power of the optical system, may be deduced from the current visual acuity value. Similarly, a defocusing power target may be deduced from the visual acuity target. The difference between defocusing power target and current defocusing power gives the necessary increment in defocusing power.

The stop criteria may be objective (e.g. visual acuity) or subjective (seen/not seen).

Practically, in the example described here, for the blurring phase, the defocusing is done through iterations till a target level of blurring has been reached, said target level being typically defined by a target visual performance.

The modification of the spherical optical power of the optical device that is arranged in front of the eye of the subject to be tested is done by iterations/steps. One step or a plurality of steps may be considered.

For example, according to the two points represented on FIG. 1, the second point—the later one—corresponding to a defocusing having reached the target level for the blurring. It is important to understand that the word "reach" is to be understood as a current defocusing being near or equal or greater, according to the case, to the target defocusing.

Figure 10:
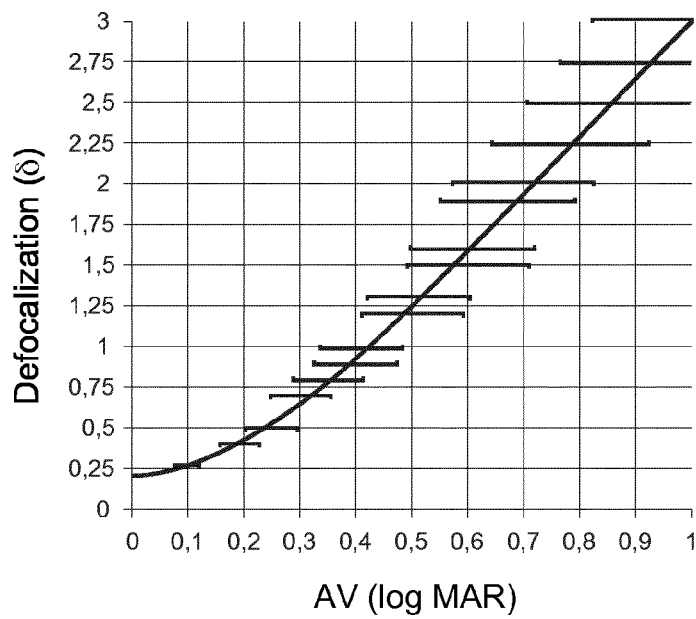
FIG. 10 represents an example of uncertainty ranges on visual acuity for given defocusing levels of the eye of a subject.
Figure 11:
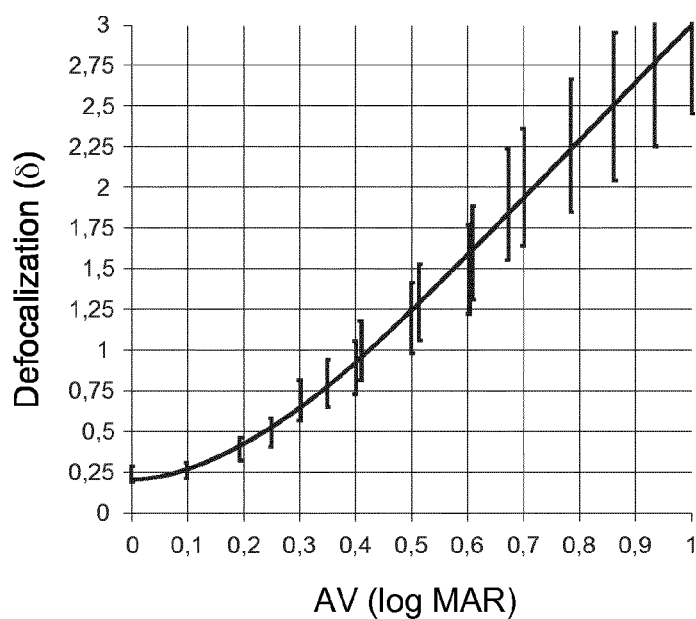
FIG. 11 represents an example of uncertainty ranges on defocusing levels of the eye for given visual acuities of a subject.

In practice, the level of blurring reached is estimated based on the visual performance of the subject, for example based on the visual acuity of the subject having his vision blurred. It is considered that the target level of blurring has been reached when the level of blurring reached is within an uncertainty range from the target level of blurring. The uncertainty range on the defocusing power placed in front of the eye of the subject depends on the visual acuity target, as shown on FIGS. 10 and 11. This is due to magnification effects of the lens and to the difficulty of perception of the subject when the vision is blurred.

For example, for a visual acuity target of $2/10^{th}$, the uncertainty range is about 0.5 diopter, whereas for a visual acuity target of $8/10^{th}$, the uncertainty range is about 0.2 diopter.

It is also important to understand that the curve of FIG. 7 on which the points are taken, has been obtained during studies on a population of subjects and, preferably, this curve is an adjusted curve based on the results of those studies and, preferably better, on a mathematical curve that is computed from a mathematical equation drafted from the results of those studies.

Having such a mathematical equation can be helpful in the implementation of an automated system, the points being computed from the equation. In a simplified implementation, tables of points can be predetermined and fetched when the blurring or unblurring processes are executed. More will be described later about the curve.

Instead of a mathematical equation, a table may be used.

Still practically, the subject is in front of a display displaying optotypes with the optical device through which the display is seen close to his/her tested eye.

Figure 2:
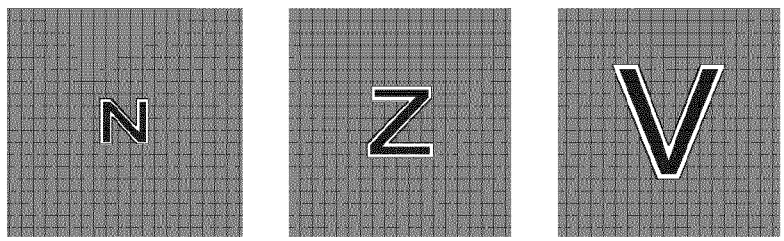
FIG. 2 represents three vanish-type optotypes.

For example, during an iteration of the display, the subject should indicate the optotype he/she is not able to recognize or the last one he/she can recognizes. On FIG. 2, three examples of optotypes corresponding to decreasing visual acuity levels reached that is, corresponding to lower visual acuity levels reached, from the left to the right, are represented.

As an example of implementation of the blurring process in a system adapted for the process:
1) The subject gazes at a vanish target,
2) The practitioner announces the guideline to the subject,
3) The practitioner increases progressively the blurring sphere by clicking on the answer of the subject in case the implementation is not fully automated.

The question to ask to the subject could be: "Can you read the letter displayed on the board/wall? I will now put lenses in front of your eye(s). Please, let me know when you do not recognize the letter anymore or when it is too blurry/fuzzy to be visible."

Instructions to the practitioner could be:

"To control accommodation, degrade the vision of your subject until a fixed visual acuity, then ask how the letter is perceived and validate the answer of the subject as indicated by clicking on the corresponding button of the system". The possible answers that could be considered are:
the letter is seen and recognized;
the letter is seen but not recognized;
the letter is imperceptible.

Instructions to the practitioner could continue with:

"Continue until the end of the test in order to obtain the precise measure of the fog value.

To cancel the last given response, click on the button.

To get back at the beginning of the test, click on the button."

Figure 3:
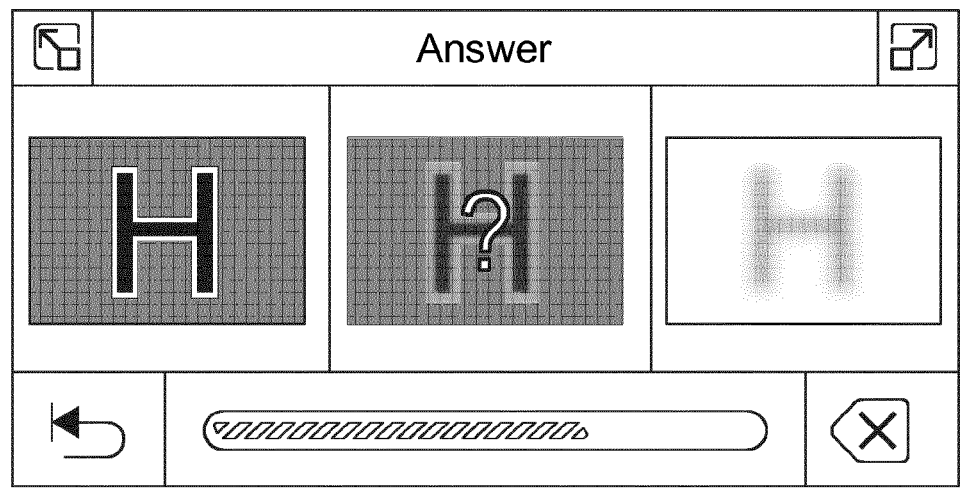
FIG. 3 represents a display for inputting results of the trials for blurring.
Figure 4:
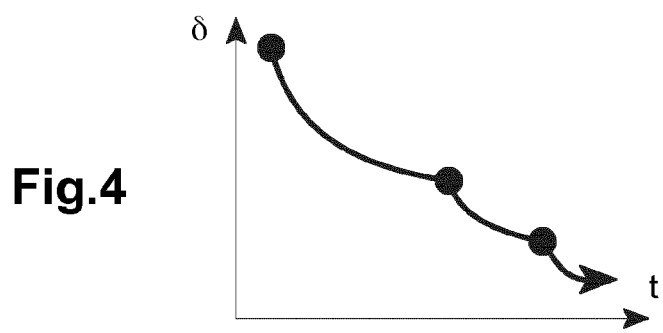
FIG. 4 represents the modification of the spherical optical power of the optical device in diopters as a function of time during iterations/steps of the method for unblurring.

The practitioner may use a computerized system that display an image such as the one of FIG. 3 for inputting results of trials during the process. It is also possible to adapt the system to the needs. For example, there is a welcome screen of the system that allows choosing the target visual acuity: 0.2 log MAR or 0.4 log MAR or 0.7 log MAR or 1.0 log MAR. It is also possible to change the type of letter to avoid memorization artefacts.

Here, preferably, the image displayed is located at a fixed distance of 6 meters from the subject. Therefore, the angle of resolution of a given optotype displayed depends only on its size on the display.

Moreover, the size of the optotype may be adjusted depending on its distance to the eye in order to accurately determine the visual acuity.

The optotype is preferably a vanish type visual target which allows a rapid assessment of the defocusing and with a method which is easily understandable by the subject.

The "Vanish Optotype" targets were first described by Howland et al in 1978. These optotypes have a pseudo-high-pass design so that the average luminance of the target is the same as the background. Thus, the stimuli disappear shortly after the resolution threshold is reached.

The center of the optotype is black (contrast of 100%) with a white perimeter (contrast of 0%) and the background of the test is gray (contrast of 50%), the thickness of the perimeter is half the thickness of the black center.

The contrast is here defined as the difference in luminance between the considered zone and its surrounding, divided by the luminance of said surrounding.

A contrast of 100% indicates that the zone is as black as possible.

A contrast of 0% indicates that the zone is as white as possible.

A contrast of 50% indicates that the zone is an intermediate grey.

In a vanish optotype, the mean luminance of the optotype including its outline is equal to the luminance of the background of the optotype.

For the visual perception or performance evaluation or visual acuity assessment, it is preferable to present to the subject a letter size slightly different from that corresponding to the target visual acuity of a 100% contrast. Boards or display characters are used, each composed of a single letter of different sizes, for example "N" to 0.3 log MAR; "Z" at 0.5 log MAR and "V" at 0.7 log MAR as represented on FIG. 2.

In other implementations, the targets could be different, in particular with different spatial frequencies or different type of symbols (C of landolt, sloan letters numbers, optotype for children). Other vanish optotypes are known, for example Auckland optotypes for children, or as seen in Frisén L. *Vanishing OptotypesNew Type of Acuity Test Letters*. Arch Ophthalmol. 1986.

Depending on the target visual performance, it is necessary to adapt the incrementation, or more generally the iteration in diopters δ, of the optical power of the blurring lens at each iteration.

This incrementation or iteration amount is defined so that a subject perceives a difference for each lens passed in front of the eyes, and also corresponds to the variability of the measurement of the visual performance carried out with different levels of blurring.

The precise determination of the blurring level is theoretically done by passing as low as 3 lenses only in front of the eyes of the wearer, and this for each size of letter. The number of iteration is preferably comprised between 0 and 3, corresponding to a process with only one step to 4 steps.

The number of steps depends on the initial conditions of the blurring method. If the subject is already blurred initially (for example, a myopic subject without correction), less than 3 steps will be needed, whereas if a lens with an excessively negative power is placed in front of the eyes, more steps might be needed to defocusing the eye of the subject.

Below is a table summarizing the characteristics of the target and the blurring lens to be proposed according to the desired (target) visual performance.

| Target Visual performance (blurring) | | Size of vanish letter displayed | Blurring lens | |
|---|---|---|---|---|
| logMAR | decimal | logMar | Small/Big increment step (in diopters) | Final added optical power** (in diopters) |
| 0.1 | 0.80 (8/10th) | 0.2/0.3* | 0.05/0.15* | 0.3 |
| 0.2 | 0.63 | 0.25 | 0.1/0.15 | 0.3 |
| 0.4 | 0.40 (4/10th) | 0.4 | 0.15/0.45 | 0.9 |
| 0.7 | 0.20 (2/10th) | 0.6 | 0.35/1.05 | 2.1 |
| 1.0 | 0.10 (1/10th) | 0.9 | 0.55/1.65 | 3.25 |

*The choice of the 0.20 δ step is based on the fact that the literature describes that the human eye can detect a monocular focus shift of this value. Given experiments done with that value, it has been decided that it could also be possible to use instead a step of 0.30 δ with the aim of generating more difference at each step while remaining consistent regarding the very variability of the measurement.
**for a subject with no astigmatism and perfect correction before blurring phase.

The big increment of spherical optical power is used typically for the first step of modifying the optical power because most of the time the patient see well through the optical system at the beginning of the test. Subsequent iterations may use the small or big increment, depending on the current visual performance determined with the current spherical optical power. The last iteration uses preferably the small increment.

FIG. 1 shows an example of the adjustment of the increment as a function of time.

For example, a objective refraction measure may be carried out before implementing the blurring phase to provide an initial value of the refraction of the eye of the subject. If this objective refraction value is close to the subjective refraction value, the first optotype presented to the subject corresponds to this objective refraction and is therefore correctly identified by the subject.

Then, a lens with a defocusing power is placed in front of the eyes of the subject, with a high increment, for example 0.45 diopter for a visual acuity target of 0.4 log MAR, optionally repeated.

Then the subject will identify the optotype, but indicate that it is slightly blurred. The defocusing power of the lens (lenses assembly or adjustable liquid lens) will be increased with a smaller increment, for example 0.15 diopter.

When the subject indicates that the optotype is no longer seen, the blurring phase ends.

If the subject has a myopia and do not wear correction lenses, his vision is already blurred at the beginning of the blurring phase. Less steps will be required to achieve the blurring phase.

For the unblurring process, the following is considered:
1) asking the subject to look at/stare/gaze a visual stimulus "in an interactive way",
2) modifying the focalization level in n steps, n being lower than the standard methods according to the personalized estimation as a function of the visual performance of the subject; preferably, n is comprised between one and three steps;
3) having a stop criteria defining that the good/target level of focalization or of visual performance has been reached.

By interactive way, it is meant that the subject is asked to read or describe the optotypes seen.

In practice, the visual stimulus is the optotype displayed in step b). The description of the perception of the visual stimulus, as detailed later, allows assessing the visual performance of the subject viewing the optotype through the optical system in step d).

It is supposed here that the vision of the subject is initially blurred, either by a blurring step performed before of because of a vision defect of the eye without compensation.

In step a), a target value of visual performance is determined. It corresponds here to a focusing target. As mentioned hereafter, the visual performance target may be determined according to different criteria, including criteria linked to the subject himself, allowing for customization of the method. The visual acuity performance is here a performance to be reached for ensuring an optimal vision to the subject, if necessary with correction lenses.

In the unblurring phase, step c) to e) are typically repeated in several iterations. Moreover, step b) is also repeated.

In the first step b) performed, the size of the optotype displayed in step c) is determined depending on the visual performance target only. Alternatively, it may be an optotype of fixed size or be determined from the target acuity value of the previous test of blurring.

In each step d), a current value of the visual performance is determined. This is done, for example, through a visual acuity test based on the description by the subject of his perception of the optotype currently displayed. Any well-known acuity test may be used.

In step e), the negative increment in spherical power of the optical system place in front of the subject is determined by taking into account the visual performance target determined in step a). It may also preferably take into account the current value of the visual performance determined in step d).

In the following iteration, in step b), a modified optotype may be determined, based on the visual performance target. This modified optotype preferably also takes into account the current value of the visual performance determined at least in the previous step d).

In the unblurring phase, the optotypes comprise preferably two lines of a given number of letters of a predetermined size corresponding to a visual acuity.

Each line comprises for example 1 to 10 letters.

The letters of each line have a predetermined size. The sizes of the letters of each of the two lines is usually different.

In step e) therefore, the size of the optotype determined may correspond to the size of only one line of letters. In step e), the number of letters or signs per line, the number of lines, the difference in size between two adjacent lines may also be determined based on the visual performance target. They may also take into account the current value of the visual performance determined at least in the previous step d).

In particular, in step b),
an uncertainty on the visual performance for a current defocusing power of the optical system is determined,
two lines of said optotypes are determined, the number of letters or signs per line, the number of lines, the difference in size between two adjacent lines being determined based on said uncertainty on the visual acuity.

This way, the number of letters or signs per line, the number of lines, the difference in size between two adjacent lines may also be determined based on the uncertainty on the visual acuity for a current defocusing power of the optical system.

If the uncertainty is higher than a given threshold, the difference in size between two adjacent lines may be increased, or the number of letters may be decreased.

If the uncertainty is lower than another given threshold, the difference in size between the two lines may be decreased, or the number of letters may be increased.

For example, for an initial step of determining the visual acuity, the subject's vision is supposed to be blurred, and it is more complicated to perform the visual acuity measurements as compared to when the subject's vision is less blurred.

For a defocusing level of the eye of 1.5 diopter, the uncertainty range of acuity is 0.2 log MAR, so the difference in size between the two adjacent lines could be 0.2 log MAR: for example a size of 0.5 log MAR and 0.7 log MAR respectively for the first and second lines.

For a defocusing of 0.5 diopter, the uncertainty range of acuity is 0.1 log MAR, so the difference in size between the two adjacent lines could be 0.1 log MAR. Moreover, one could display more letters on each line to have a more precise measurement.

For the unblurring (or defogging) phase, a predefined focusing goal to attain is chosen for the examination of the subject and an optotype is arranged in front of the subject.

This predefined focusing goal corresponds to, that is to say is determined based on, the target visual acuity.

Now examples of the unblurring process are described more in details.

The unblurring of the invention is a simple process allowing the search of the sphere by the measurement of the visual performance when the visual system is in situation of defocusing. For this, the practitioner will perform a measurement of visual performance, that is to say, will determine for example the visual acuity, and unblurring will automatically be performed according to the state of defocusing estimated based on the visual acuity determined.

Typically, in step a), the value of the predefined focusing goal, also called in the following visual acuity target or focusing target, is fixed at a value of visual acuity equal to $10/10^{th}$. The final set of optotypes displayed at the end of the unblurring method should therefore test the vision for this visual acuity.

The visual acuity target may be adapted depending on the purpose of this unblurring phase in the subject eye examination for example.

It may be indeed different if the unblurring phase is performed before checking the spherical refraction of the eye with another test, before checking the astigmatism of the eye, for example cylinder and/or axis of the eye, or before performing a last test before prescribing the refraction correction.

Before checking the spherical refraction of the eye with another test, the visual performance target may be a visual acuity with still a slight blur of $8/10^{th}$ for example.

Before checking the astigmatism of the eye, the visual performance target may be a visual acuity corresponding to an absence of blur with no accommodation, for example of 10/10th.

Before performing a last test before prescribing the refraction correction, the visual performance target may be set to a maximum value, for example $12/10^{th}$, corresponding to the average maximum visual acuity.

The value of the visual performance target may also be adapted depending on personal features of the subject, such as the estimated maximum acuity of the subject. This maximum visual acuity may be estimated depending on age, ametropia, geographical origins of the subject and ocular history of the subject, such as ocular diseases (cataract), past prescriptions etc.

The visual acuity is indeed known to decrease while the age of the subject increases because of a decrease of the transparency of the eye and a decreased efficiency in the treatment of the signal from the retina.

The visual acuity target may for example be set to $8/10^{th}$ for a senior person over 60 years and $12/10^{th}$ for young adults.

It is also known that the ocular anatomy is slightly different depending on geographical origins of the subject, as known from Blake, CR; Lai, WW; Edward, DP in Racial and Ethnic Differences in Ocular Anatomy. International ophthalmology, 2003. The visual acuity target for Asian subjects could be set as $8/10^{th}$, as this is the average maximal value observed for subject with these origins. The visual acuity target would be set to $10/10^{th}$ for Caucasian subjects.

The visual acuity of a subject also depends on the pupil diameter: the maximum visual acuity that can be reached increases with an increased pupil diameter up to a pupil diameter of 3 millimeters, then slowly decreases for pupil diameter over 3 millimeters, because of the optical aberrations, and stabilizes to an intermediate value. Therefore the visual acuity target could be determined depending on the pupil diameter in the lighting conditions of the process.

The ametropia has also an influence, as discussed in the following paragraphs, because the correction lens used in front of the eye during the method according to the invention will tend to increase or decrease the size of the optotypes. The visual acuity target may therefore be smaller for subjects with myopia as the correction lens will decrease the size of the optotype, and higher for subjects with hyperopia as the correction lens will tend to increase the size of the optotype.

The value of the visual performance target may also be determined depending on environmental parameters, such as parameters of the measurement set-up. Lighting conditions may for example have an impact: the contrast of the optotype and therefore its perception is modified by lighting.

For example, it may depend on the distance between the eye of the subject and the optical system comprising blurring/unblurring lense and/or correction lenses placed in front of the eye of the subject.

This distance may indeed influence the optical magnification through the optical system and therefore the visual acuity determined.

A convex lens enlarges an object seen through his convex lens, whereas a concave lens shrinks the same object seen through the concave lens. In other words, the image of an object seen through a convex lens is bigger than the real object, whereas the image of an object seen through a concave lens is smaller.

The effect (enlargement or shrinkage) depends on the power and/or width of the lens, and of the distance between the lens and the eye of the subject. For example, a subject with a high degree of myopia, with a correction lens of −8 diopters placed at 20 millimeters from the eye of the subject would have a visual acuity target of about $8/10^{th}$ or $10/10^{th}$ if the lens is placed at 10 millimeters from the eye, whereas a subject with hyperopia, the visual acuity target could be set at $12/10^{th}$ as the correction lens placed in front of the eye enlarges the image of the object.

It is preferred to perform the unblurring phase in three iterations when the subject has been previously blurred for a visual acuity of 0.4 log MAR. This unblurring method may nevertheless be adapted according to the level of initial blur reached after the blurring phase, the target visual performance, etc. An unblurring phase performed in one to five steps is preferred.

The main objective of this is that the subject reaches a predefined visual performance using only three unblurring lenses or within a predetermined number of unblurring lenses and not a variable number of unblurring lenses as in the standard method.

Figure 5:
FIG. 5 represents an acuity plate displaying optotypes of the optotype type, with the corresponding visual acuity in log MAR.

For that purpose:
1) The subject gazes at a visual acuity plate such as the one represented FIG. 5 and displaying optotypes,
2) the visual acuity is assessed through a validation of a line when 4 out of 5 letters of this line are correctly read/understood, the line corresponding to the assessed visual acuity.
3) Automatically, the unblurring lens is placed in front of the subject's eye(s) and the visual acuity plate corresponding to the target performance is presented,
4) A new visual acuity plate is displayed;
5) If the target visual performance is not reached, the practitioner re-asses the visual performance until the expected result is reached.

Preferably, as already mentioned, during unblurring, two lines of a given number of optotypes are displayed. The size of optotypes of each line correspond to a different visual acuity.

During this iterative process, the following instructions may be directed to the subject: «What is the smallest line of letters that you can decipher even if it is unclear: without squinting and without closing the eye behind the cache»

If two lines of otptotypes are displayed, the instructions may be: "can you read the bottom line? If no, can you read the upper line?"

In case the target value of the visual performance cannot be reached, that is to say the current value of visual performance remains stable or departs from the target value (an extremum value of the visual performance being reached), then the repetition of steps c) to f) is stopped.

In this case, the successively added negative spherical optical powers determined at step e) for all the repetitions before stabilization or deviation from the target value are added up together to define an unblurring spherical optical power which provide the best visual acuity.

This unblurring spherical optical power is the value of the spherical refraction correction needed, or in other word the spherical refraction correction that gives the best visual acuity to the subject.

On his/her side, the practitioner may have to follow the following instructions:
"Approach the sphere precisely.
Ask to read the lines of letters.
Continue until the progress bar is complete. The test ends when the subject reaches a visual acuity of at least 10/10th. Manually modify the sphere if necessary.
Validate the subject's response as indicated by clicking on the corresponding buttons.
The possible answers are:
All lines are read
Part of the lines is read
No line is read
The sphere and the sharpness plate are then modified so that the subject obtains a visual acuity greater than 10/10th. You can also change the sphere manually with the corresponding buttons.
Continue this way until you exit the test to get close to the sphere.
To cancel the last answer, press the corresponding button. To return to the beginning of the test, press the corresponding button. To open the shutters detailing the progress of the test, click on the corresponding button.

To cancel the last answer given, press the corresponding button. To return to the beginning of the test, press the button.

To open the sections detailing the progress of the test, click on the corresponding button.»

Figure 6:
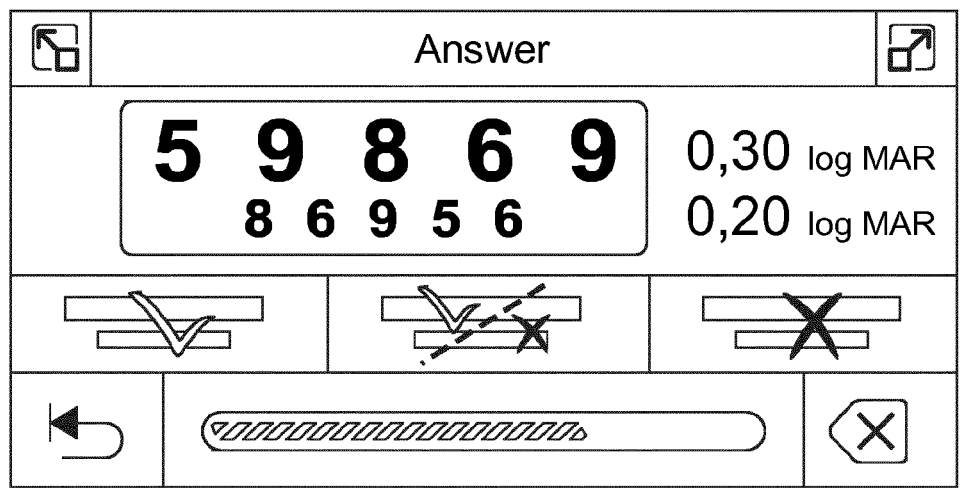
FIG. 6 represents a display for inputting results of the trials for unblurring with the corresponding visual acuity in log MAR.

The practitioner may use a computerized system that display an image such as the one of FIG. 6 for entering results during the process. This may also be used by the subject to directly enter the results in the computerized system.

It is also possible to customize the system. In particular, it is possible to choose the target of visual performance to which it is possible to take the subject. It is also possible to perform a random change of the optotypes to avoid the effects of memorization.

It is now explained how the amounts of change of optical power of the optical device at each iteration for the blurring and unblurring processes have been determined.

The scientific literature presents numerous papers describing laws that correlate the visual performance achieved with different types and levels of defocusing. The method of the invention is based on these laws, calculating the unblurring lens to be proposed according to the measured visual performance and the target visual performance that it is expected to reach in a few steps.

Several authors have described models for estimating the defocus level of the visual system as a function of measured visual acuity. The most famous are Swaine, Raasch, Blendowske, Gomez.

The focusing step, and therefore the determination of the increment in spherical power of the optical system may be achieved taking into account any one of several models to determine the thresholds of vision. These models are described in the following publications: W. Swaine, «*The relation of visual acuity and accommodation to ametropia*» Optician (1925); R. Blendowske, «*Unaided visual acuity and blur: a simple model*» Optom. Vis. Sci. 92, e121-e125 (2015); T. W. Raasch, «*Spherocylindrical refractive errors and visual acuity*» Optom. Vis. Sci. 72, 272-275 (1995); J. Gomez-Pedrero et J. Alonso, «*Phenomenological model of visual acuity*», J Biomed Opt 21(12) 125005 (2016).

These models are based on different criteria and are not universal.

According to the invention, the amounts of change of optical power of the optical device at each iteration for the blurring and unblurring processes may take into account different parameters such as visual features: astigmatism, axis, pupil diameter, personal features such as age or sex, or environmental such as lighting conditions.

According to the invention, it is proposed to use a model represented on FIG. 7 with vertically the defocusing $\delta$ and horizontally the visual acuity AV (log MAR). This model of FIG. 7 follows the Swaine law for very low defocus levels (0 $\delta$ to 0.5 $\delta$), Gomez law for small defocus levels (0.5 $\delta$ to 1.75 $\delta$), and the Blendoswke law for the strong defocus levels (>1.75 $\delta$)

This model of FIG. 7 has been approximated with the following equation:

Spherical defocusing of the eye=$-2{,}2236(VA)^3 + 4{,}7411(VA)^2 + 0{,}263\ (VA) + 0{,}2039$ Where VA=Visual Acuity (in log MAR).

This equation is used in the automated system for computing the added or subtracted amount of optical power to the optical device at each iteration of the processes . . . .

Again, the main objective is that the subjects reach a predefined visual acuity by going through a definite number of unblurring lenses and not a variable number as in the standard method.

For this, the proposed method comprises determining the visual acuity of the subject, estimating the spherical defocusing state of the eye of the subject following the blurring step using the equation stated above and the visual acuity determined. The calculation of the powers of the unblurring lenses to be used is performed to achieve intermediate acuities allowing a better estimate of the defocusing state value.

As an example, it is used a reduced value (70%) of the actual unblurring lens calculated to be recommended to achieve the visual performance targeted so as not to obtain a too concave value. The spherical values were calculated and then rounded to the hundredth of a diopter. This choice also depends on the variability of the measurement of the blurred visual performance. The spherical values were calculated then rounded to the tenth of a diopter.

The number of steps depends on the initial conditions and the target value of visual performance. If the subject is really blurred initially (for example, a high myopic subject without correction), 3 steps will be needed, whereas if he started without blur, or with a little one (myopic subject with correction), in less step are necessary because the visual acuity target will be obtained.

Depending on the visual performance with blurring and the visual performance that the practitioner wishes to achieve, it is recommended to perform the test in a number of iterations/steps (=Number of unblurring lenses): from one to five iterations and preferably two or three iterations.

As examples for blurring:

Starting blurring at 1.0 log MAR and with three iterations/steps:
1) Unblur 70% of the value to reach 0.4 log MAR
2) Unblur 70% of the value to reach 0.0 log MAR
3) Unblur 100% of the value to reach 0.0 log MAR (if not previously reached)

Starting blurring at 0.7 log MAR and with three iterations/steps:
1) Unblur 70% of the value to reach 0.3 log MAR
2) Unblur 70% of the value to reach 0.0 log MAR
3) Unblur 100% of the value to reach 0.0 log MAR (if not previously reached)

Blurring start at 0.4 log MAR and with two iterations/steps:
1) Unblur 70% of the value to reach 0.0 log MAR
2) Unblur 100% of the value to reach 0.0 log MAR (if not previously reached)

If the starting acuity is at 0.2 log MAR, it is done with only one unblurring lens:
1) Unblur 70% of the value to reach 0.0 log MAR As another example but for the unblurring:
1) If the blurred visual acuity of the subject is 0.7 log MAR, then the unblurring is done with 0.91 $\delta$.
2) if the blurred visual acuity of the subject is now 0.5 log MAR, then the unblurring is done with 0.73 $\delta$.
3) if the blurred visual acuity of the subject is 0.1 log MAR, we unblur 0.18 $\delta$.

The visual acuity is 0.0 log MAR and it took only three lenses to reach the acuity of 0.0 log MAR.

In a particular case, in the unblurring method, if the target of visual acuity is not reached, it is proposed that the altering value of spherical optical power added at the last step e) is positive to be sure that the subject has his maximum of visual performance with the maximum spherical power.

For example, if the same visual acuity is measured for three different powers of the lens or lenses placed in front of the subject, the method is stopped and the first value of power with the same acuity is taken into account for determining the spherical refraction correction need of the subject.

According to another example, If the answer of the subject indicates twice that the visual acuity is less than the visual acuity measured previously, the method is stopped and the first value of power with the best visual acuity is taken into account.

According to another example of the method according to the invention, a final visual acuity target of for example $10/10^{th}$ is to be achieved.

In a first embodiment:
when the measured visual acuity is less than $2/10^{th}$, a intermediate visual acuity target is set to $4/10^{th}$, corresponding to a first step toward the final visual acuity target. The corresponding defocusing power is determined with the equation Eq mentioned previously and applied. The optotypes with a size corresponding to the visual acuity $4/10^{th}$ are displayed;
when the measured visual acuity is more than $2/10^{th}$ and less than $4/10^{th}$, a intermediate visual acuity target is set to $5/10^{th}$, corresponding to a first step toward the final visual acuity target. The corresponding defocusing power is determined with the equation Eq mentioned previously and applied. The optotypes with a size corresponding to the visual acuity $5/10^{th}$ are displayed;
when the measured visual acuity is more than $4/10^{th}$ and less than $8/10^{th}$, the visual acuity target is said final visual acuity target. The corresponding defocusing power is determined with the equation Eq mentioned previously and applied. The optotypes with a size corresponding to the final visual acuity are displayed;
when the measured visual acuity is more than $8/10^{th}$, the visual acuity target is said final visual acuity target. The defocusing power is set to 0.2 diopter and applied. The optotypes with a size corresponding to the final visual acuity are displayed.

When using optotype displayed in two lines of different sizes, the optotypes with the size corresponding to the visual acuity looked for are placed on the bottom line.

In a second embodiment:
when the measured visual acuity is more than $2/10^{th}$ and less than $4/10^{th}$, the visual acuity target is said final visual acuity target. The corresponding defocusing power is determined with the equation Eq mentioned previously and 70% of this defocusing power is applied. The optotypes with a size corresponding to the final visual acuity are displayed;
when the measured visual acuity is more than $4/10^{th}$ and less than $8/10^{th}$, the visual acuity target is said final visual acuity target. The corresponding defocusing power is determined with the equation Eq mentioned previously and applied. The optotypes with a size corresponding to the final visual acuity are displayed;
when the measured visual acuity is more than $8/10^{th}$, the visual acuity target is said final visual acuity target. The defocusing power is set to 0.2 diopter and applied. The optotypes with a size corresponding to the final visual acuity are displayed.

A maximum total value of defocusing power is for example 1.6 diopters. In the examples described here, the visual performance target is a visual acuity target. However, other targets may be considered, such as: low contrast acuity, dynamical acuity, children's acuity, speed of reading, sensitivity to contrasts.

The spherical power of the correction lenses needed by the subject in order to achieve the visual acuity performance target is determined based on the spherical power of the optical system at the end of the unblurring phase, that is, when the visual performance target is achieved.

The invention claimed is:

1. A method for altering the visual performance of a subject using an optical system arranged in front of at least one eye of the subject and comprising successive steps of:
   a) choosing a target value of visual performance, said target value of visual performance being a predefined visual acuity;
   b1) determining a size of an optotype depending on said target value of visual performance;
   b2) determining an optotype having the determined size;
   c) displaying the optotype determined in step b2) to the subject in such a way that said optotype is visible by the subject through said optical system;
   d) assessing the visual performance of the subject viewing the optotype displayed in step c) through the optical system; and
   e) determining an altering value of spherical optical power depending on said target value of visual performance and applying said altering value of spherical optical power to the optical system, said altering value being positive or negative.

2. The method according to claim 1, further comprising a step of:
   f) assessing the visual performance of the subject after step e), and defining the result of this assessment as a current value of visual performance,
   wherein steps c), d), e), and f) are repeated until said current value of visual performance reaches said target value of visual performance or remains stable or departs from the target value, and
   wherein said altering value of spherical optical power added to the optical system at step e) is determined as a function of said target value of visual performance and of said current value of visual performance.

3. The method according to claim 1,
   wherein the goal of the alteration is to blur the vision of the subject, and
   wherein the altering value of spherical optical power is positive, so as to put said subject in myopic conditions, with a blurred vision and a relaxed accommodation.

4. The method according to claim 3, wherein said subject wears an ophthalmic correction in order to recognize the optotype during step d).

5. The method according to claim 3, wherein:
   at step d), a step takes place of asking the subject whether said optotype is visible or imperceptible through said optical system, and
   at step e), a step takes place of adding a positive altering value of spherical optical power, said altering value being determined as a function of the answer of the subject, of the previously added altering value and said target value of visual performance.

6. The method according to claim 5, wherein, at step e), said altering value is different whether the subject answers that:
   he/she sees and recognizes the optotype, or
   he/she sees and does not recognize the optotype.

7. The method according to claim 1, wherein the optotype is a vanish-type optotype.

8. The method according to claim 7, wherein, at step a), said vanish-type optotype is chosen randomly among the following vanish-type letters: D, H, K, N, R, S, V, and Z.

9. The method according to claim 3, further comprising a step of:
f) assessing the visual performance of the subject after step e), and defining the result of this assessment as a current value of visual performance,
wherein steps c), d), e), and f) are repeated until said current value of visual performance reaches said target value of visual performance or remains stable or departs from the target value,
wherein said altering value of spherical optical power added to the optical system at step e) is determined as a function of said target value of visual performance and of said current value of visual performance, and
the size of the optotype remaining the same while steps c), d), e), and f) are repeated.

10. The method according to claim 1, wherein:
the effect of the alteration consists in unblurring the vision of the subject so as to reach said target value of visual performance for one or both eyes of the subject,
said optical system initially has an added altering value of spherical optical power such that the subject is initially in myopic conditions, with a blurred vision and a relaxed accommodation,
the assessment of the visual performance of the subject viewing the optotype through the optical system at step d) allows deducing a level of defocusing of the subject, and
the altering value of spherical optical power added at step e) is negative for unblurring the vision of the subject and is determined from the target value of visual performance and from said level of defocusing.

11. The method according to claim 10, wherein said level of defocusing and said visual performance are correlated through a mathematical formula.

12. The method according to claim 10, further comprising a step of:
f) assessing the visual performance of the subject after step e), and defining the result of this assessment as a current value of visual performance,
wherein steps c), d), e), and f) are repeated until said current value of visual performance reaches said target value of visual performance or remains stable or departs from the target value,
wherein said altering value of spherical optical power added to the optical system at step e) is determined depending on said target value of visual performance and of said current value of visual performance, and
wherein step b) is repeated, and at each step b), the size of the optotype is determined depending on said target value of visual performance and of said current value of visual performance.

13. The method according to claim 10, wherein, in step b), an uncertainty on the visual performance for a current defocusing power of the optical system is determined, and
two lines of said optotypes are determined, the number of letters or signs per line, the number of lines, the difference in size between two adjacent lines being determined based on said uncertainty on the visual acuity.

14. The method according to claim 1, wherein said value of the visual acuity target determined in step a) is adapted depending on one of the following:
a purpose of the blurring or unblurring phase in the subject eye examination,
personal features of the subject, and
environmental parameters.

15. The method according to claim 1, wherein said value of the visual acuity target is determined in step a) by taking into account a model linking the defocusing level of the eye to the visual performance of the eye, this model being built on data collected while performing the blurring/unblurring phase on subjects and/or thanks to computer learning algorithms.

16. A method for measuring a spherical refraction correction need of a subject, comprising:
implementing a method for blurring the vision of said subject; and
implementing a method for unblurring the vision of said subject so as to reach a target value of visual performance for one or both eyes of the subject, said method for unblurring the vision of said subject using an optical system arranged in front of at least one eye of the subject and comprising successive steps of:
b) determining an optotype,
c) displaying the optotype determined in step b) to the subject in such a way that said optotype is visible by the subject through said optical system,
d) assessing the visual performance of the subject viewing the optotype displayed in step c) through the optical system,
e) adding an altering value of spherical optical power to the optical system, said altering value being positive or negative,
wherein, before step b), a step is carried out of:
a) choosing a target value of visual performance,
wherein, at step b), said optotype has a size which is determined depending on said target value of visual performance,
wherein, at step e), said altering value of spherical optical power is determined depending on said target value of visual performance,
wherein said optical system initially has an added altering value of spherical optical power such as the subject is initially in myopic conditions, with a blurred vision and a relaxed accommodation,
wherein the assessment of the visual performance of the subject viewing the optotype through the optical system at step d) allows deducing a level of defocusing of the subject,
wherein the altering value of spherical optical power added at step e) is negative for unblurring the vision of the subject and is determined from the target value of visual performance and from said level of defocusing,
wherein a further step is carried out of:
f) assessing the visual performance of the subject after step e), and defining the result of this assessment as a current value of visual performance,
wherein steps c), d), e), and f) are repeated until said current value of visual performance reaches said target value of visual performance or remains stable or departs from the target value,
wherein said altering value of spherical optical power added to the optical system at step e) is determined as a function of said target value of visual performance and of said current value of visual performance,
said initial myopic conditions resulting from the implementation of said method for blurring,
wherein the successively added negative altering values of spherical optical power of the successive iterations of steps e) are added up together until said current value of visual performance reaches said target value of visual performance, or before the current value of visual performance remains stable or departs from the target value, for defining an unblurring spherical optical power, and wherein the spherical refraction correction need is determined based on said unblurring spherical optical power.

17. The method according to claim 1, wherein said value of the visual acuity target determined in step a) is adapted depending on one of the following:
a purpose of the blurring or unblurring phase in the subject eye examination,
personal features of the subject,
environmental parameters,
wherein the goal of the alteration is to blur the vision of the subject, and
wherein the altering value of spherical optical power is positive, so as to put said subject in myopic conditions, with a blurred vision and a relaxed accommodation.

18. An optical system for implementing a method according to claim 1, said optical system comprising an optical device configured to be placed in front of at least one eye of the subject and to impart an additional spherical optical power to this eye, wherein said spherical optical power is adjustable.

19. The method according to claim 2,
wherein the goal of the alteration is to blur the vision of the subject, and
wherein the altering value of spherical optical power is positive, so as to put said subject in myopic conditions, with a blurred vision and a relaxed accommodation.

20. The method according to claim 4, wherein:
at step d), a step takes place of asking the subject whether said optotype is visible or imperceptible through said optical system, and
at step e), a step takes place of adding a positive altering value of spherical optical power, said altering value being determined as a function of the answer of the subject, of the previously added altering value and said target value of visual performance.

21. A method for altering the visual performance of a subject using an optical system arranged in front of at least one eye of the subject, the method comprising successive steps of:
a) choosing a target value of visual performance taking into account the visual characteristics of the subject, said target value of visual performance being a predefined visual acuity;
b1) determining a size of an optotype depending on said target value of visual performance;
b2) determining an optotype having the determined size;
c) displaying the optotype determined in step b2) to the subject in such a way that said optotype is visible by the subject through said optical system;
d) assessing the visual performance of the subject viewing the optotype displayed in step c) through the optical system; and
e) determining an altering value of spherical optical power depending on said target value of visual performance and applying said altering value of spherical optical power to the optical system, said altering value being positive or negative.

* * * * *